US006503707B1

(12) United States Patent
Baxter-Lowe

(10) Patent No.: US 6,503,707 B1
(45) Date of Patent: Jan. 7, 2003

(54) METHOD FOR GENETIC TYPING

(75) Inventor: Lee Ann Baxter-Lowe, New Berlin, WI (US)

(73) Assignee: The Blood Center Research Foundation, Inc., Milwaukee, WI (US)

( * ) Notice: Subject to any disclaimer, the term of this patent is extended or adjusted under 35 U.S.C. 154(b) by 1643 days.

(21) Appl. No.: 08/650,965

(22) Filed: May 21, 1996

Related U.S. Application Data

(63) Continuation of application No. 08/142,214, filed on Oct. 25, 1993, now abandoned, which is a continuation-in-part of application No. 08/025,038, filed on Mar. 1, 1993, now Pat. No. 5,545,526, which is a continuation-in-part of application No. 07/544,218, filed on Jun. 27, 1990, now abandoned, application No. 08/650,965, which is a continuation-in-part of application No. 08/057,957, filed on Apr. 8, 1993, now Pat. No. 5,702,885, which is a continuation of application No. 07/544,218, filed on Jun. 27, 1990, now abandoned.

(51) Int. Cl.$^7$ ............................ C12Q 1/68; C12P 19/34
(52) U.S. Cl. .......................................... 435/6; 435/91.2
(58) Field of Search ..................... 435/6, 91.2

(56) References Cited

U.S. PATENT DOCUMENTS

| | | | | |
|---|---|---|---|---|
| 4,582,788 A | | 4/1986 | Erlich ............................ | 435/6 |
| 4,683,202 A | | 7/1987 | Mullis ............................ | 435/91 |
| 4,824,776 A | * | 4/1989 | Heller ............................ | 435/6 |
| 5,468,613 A | * | 11/1995 | Erlich et al. .................... | 435/6 |

FOREIGN PATENT DOCUMENTS

| | | | |
|---|---|---|---|
| EP | 0297379 | * | 1/1989 |

OTHER PUBLICATIONS

Eliaou et al., "Generic HLA–DRB1 gene oligotyping by a nonradioactive reverse dot–blot methodology", Human Immunology 35: 215–222, 1992.*

Mitchell et al, Analytical Biochem, V. 178, (1989), 239–42.*
Matthews et al, Analytical Biochem, V. 169 (1988), 1–25.*
Angelini, *Proc. Natl. Acad. Sci. USA*, 83:4489–4493, 1986.
Opelz, *The Lancet*, 338:461–463, 1991.
Mickelson, *Tissue Antigens*, 41:86–93, 1993.
Scharf, *Science* 233:1076–78.
Cox, *Am. J. Hum. Gen.*, 43:954–63, 1988.
Tiercy, *Proc. Natl. Acad. Sci. USA*, 85:198–202, 1988.
Tiercy, *Human Immunol.*, 24:1–14, 1989.
Saiki, *Nature*, 324:163–166, 1986.
Bugawan, *J. Immunol.*, 141:4024–4030, 1988.
Gyllensten, *Proc. Natl. Acad. Sci. USA*, 85:7652–7656, 1988.
Molkentin, *Hum. Immunol.*, 31:114, 1991.
Hultman, *Nucl. Acids. Res.*, 17:4937–4946, 1989.
Fry et al., *BioTechniques*, vol. 13, No. 1, pp. 124–131, 1992.

* cited by examiner

*Primary Examiner*—Scott D. Priebe
(74) *Attorney, Agent, or Firm*—Philip G. Meyers

(57) ABSTRACT

A method for genetic typing includes the steps of amplifying a genetic sequence of a subject to obtain amplified DNA, which genetic sequence occurs naturally in two or more genetic types, bringing a sample of the amplified DNA into contact with an oligonucleotide probe bound to a support under stringent hybridizing conditions, which oligonucleotide probe hybridizes specifically with DNA having a sequence of one of the genetic types and not with DNA having a sequence of the other genetic types, removing unbound amplified DNA, for example, by washing the support, and analyzing the sample to determine if the one genetic type associated with the probe is present. Use of a solid support such as microbeads provides a more rapid method for identifying polymorphic nucleotide sequences of polymorphic genes, such an HLA sequences.

16 Claims, No Drawings

METHOD FOR GENETIC TYPING

This is a continuation of application Ser. No. 08/142,214 filed Oct. 25, 1993 abandoned.

This application is a continuation-in-part of U.S. Ser. No. 08/025,038, filed Mar. 1, 1993, now U.S. Pat. No. 5,545,526 which was a continuation-in-part of U.S. Ser. No. 07/544,218, filed Jun. 27, 1990, abandoned, and is also a continuation-in-part of U.S. Ser. No. 08/057,957, filed Apr. 8, 1993, now U.S. Pat. No. 5,702,885, a continuation of U.S. Ser. No. 07/544,218, filed Jun. 27, 1990, abandoned.

This invention was made with Government support, and the Government has certain rights in the invention.

FIELD OF THE INVENTION

The invention relates to a method for genetic typing, particular to a method for identifying nucleotide sequences of polymorphic genes such as genes coding for human leukocyte antigens.

BACKGROUND OF THE INVENTION

The major histocompatibility complex of humans is a cluster of genes occupying a region located on the sixth chromosome. Human leukocyte antigen (HLA) genes are highly polymorphic and code for human leukocyte antigens whose structural variation is a major factor influencing tissue transplantation, immunity and autoimmunity. The polymorphic HLA proteins have been designated HLA-A, -B, -C, -DR, -DQ and -DP. The HLA-A, -B, and -C proteins are described as class I HLA proteins and are characterized by a polymorphic chain, alpha, and a nonpolymorphic chain, beta 2 microglobulin. The HLA-DR, -DQ and -DP proteins are classified as class II HLA proteins and are also comprised of two polypeptide chains, an alpha chain and a highly polymorphic beta chain. These HLA-D-region proteins are encoded by loci designated HLA-DRA, -DRB1, -DRB3, -DRB4, -DRB5, -DQA1, -DQB1, -DPA1 and -DPB1. HLA-DRA, -DQA1 and -DPA1 are much less polymorphic than HLA-DRB1, DQB1 and -DPB1.

The HLA proteins encoded by the polymorphic genes of the different HLA loci have previously been typed by serological methods. The major drawbacks to such HLA typing, are the complexity of the sera and the lack of widespread availability of standard sera necessary to conduct the tests. Serological HLA-typing techniques require the presence of detectable levels of HLA proteins on the surface of lymphocytes. In some cases, such as HLA-deficient severe combined immunodeficiency (SCID) and cellular depletion due to chemotherapy, the levels of the HLA proteins are inadequate to achieve reliable HLA typing. Another limitation of traditional serological typing methods is the inability to resolve all functionally important HLA proteins. These circumstances have prompted the development of methods for analysis of HLA polymorphism at the genetic level, as described by Bidwell, *Immunology Today* 9: 18–23 (1988), and by Angelini et al., Proc. *Nat'l Acad. Sci., USA* 83: 4489–93 (1986).

Non-serological HLA typing methods have been proposed to overcome drawbacks with serological typing. One such method involves the use of DNA restriction fragment length polymorphism (RFLP) as a basis for HLA typing. See Erlich, U.S. Pat. No. 4,582,788, Opelz et al., *Lancet* 338:461–463 (1991) and Mickelson et al. Tissue Antigens 41:86–93 (1993). RFLP analysis, however, fails to differentiate between certain alleles that are known to exist in the population (e.g., subtypes of HLA-DR4), and thus, cannot be used to distinguish certain combinations of alleles. Moreover, its practical usefulness is limited because the procedures involved are laborious, and difficulties arise in interpreting data for certain combinations of alleles.

Some typing methods, including RFLP-based analyses, utilize labelled oligonucleotides to identify specific HLA nucleotide sequences. In particular, the use of oligonucleotide probes has been found advantageous in HLA-DR typing to identify HLA-proteins which are not detectable serologically. See Angelini et al., supra; Scharf et al., *Science* 233: 1076–78; Cox et al., *Am. J. Hum. Gen.*, 43: 954–63 (1988); Tiercy et al., Proc. *Nat'l Acad. Sci. USA* 85: 198–202 (1988), *Human Immunol.* 24: 1–14 (1989). For example, sequence-specific oligonucleotide probe hybridization (SSOPH) can discriminate single base pair mismatches, which is equivalent to detecting a single amino acid polymorphism in HLA proteins.

More recently, utilizing the polymerase chain reaction (PCR) process, as described in U.S. Pat. No. 4,683,202, researchers have used sequence-specific oligonucleotide ("SSO") probe hybridization to perform HLA-Class II typing. The method entails amplifying a polymorphic region of an HLA locus using PCR, contacting the amplified DNA to a sequence-specific oligonucleotide probes under hybridizing conditions, and detecting hybrids formed between the amplified DNA and the sequence-specific oligonucleotide probes. Alleles of all class II HLA and some class I HLA genes have been identified in the aforementioned manner. See Saiki et al., *Nature*, 324:163–166, 1986, Bugawan et al., *J. Immunol.*, 141:4024–4030, 1988, and Gyllensten et al., *Proc. Natl. Acad. Sci. USA*, 85:7652–7656, 1988.

In the parent application, Ser. No. 08/025,038, filed Mar. 1, 1993, a two-step method is described for resolving HLA-DQB1 and HLA-DRB1 alleles more fully. The described two-step method comprises a low resolution, locus-specific amplification assay followed by a high resolution, intra-locus specific assay. Although highly accurate, the two-step method is consuming and labor intensive because it requires at least two amplification steps. See also Molkentin et al., *Hum. Immunol.*, 31:114, 1991. A need exists, therefore, for a more rapid and easily implemented approach to identifying nucleotide sequences of polymorphic genes, and in particular, for identifying nucleotide sequences of polymorphic genes coding for human leukocyte antigens. Solid supports such as Dynabeads (microbeads available from Dynal) have been used for purification of mixtures prior to sequencing. See Hulman et al. *Nucl. Acids. Res.* 17:4937–4946 (1989) and Fry et al., *BioTechniques* Vol. 13, No. 1, p. 124–131 (1992). However, no such method has been used for the purpose of typing an unknown sample.

SUMMARY OF THE INVENTION

A method for genetic typing according to the invention includes the steps amplifying a genetic sequence, which genetic sequence may occurs naturally in two or more genetic types, separating from a mixture of amplified DNA a sample of one type substantially free of DNA of the other types, and then optionally further analyzing the sample to confirm or further characterize the DNA of the selected type. The genetic type will commonly be a basic type that includes two or more specific alleles, in which case the step of further analyzing the sample may further entail determining which allele of the basic type is present. HLA subtypes that can be differentiated using a single oligonucleotide probe, such as HLA-DR1, DR2, DR3, etc. represent a basic genetic type within the meaning of the invention. For purposes of typing according to the invention, references to DNA should also be understood to include RNA sequences, for which it is generally necessary to first prepare the corresponding cDNA.

A preferred method for genetic typing according to the invention includes the steps of:

(a) amplifying a genetic sequence of a subject to obtain amplified DNA, which genetic sequence occurs naturally in two or more genetic types;

(b) bringing a sample of the amplified DNA into contact with an oligonucleotide probe bound to a support under stringent hybridizing conditions, which oligonucleotide probe hybridizes specifically with DNA having a sequence of one of the genetic types and not with DNA having a sequence of the other genetic types;

(c) removing unbound amplified DNA, for example, by washing the support; and (d) analyzing the sample to determine if the one genetic type is present.

"Genetic type" as used herein refers to virtually any naturally occurring nucleotide sequence which exists in a number of variations or alleles. HLA types, such as HLA DP, DQ and DR alleles, are examples. Amplification as carried out in step (a) need be only locus specific, not sequence specific. Step (a) may also be carried out using the combined products of two or more locus-specific amplifications, or the combined products of two or more sequence-specific amplifications. For purposes of the present invention, locus-specific amplification refers to amplification of all or a major portion of a locus such that most if not all naturally-occurring alleles within that locus would be amplified. Primers for locus-specific amplification have sequences corresponding to sites at which little or no polymorphism occurs. Primers for sequence-specific amplification include one primer having a sequence corresponding to a polymorphic site comprising a basic type, allele or group of alleles having a common polymorphism so that only sequences having the polymorphism are amplified.

The step of analyzing the sample may be carried out in a number of different ways. For example, prior to step (d), the bound amplified DNA may be denatured and removed from the support under conditions effective to isolate a sample of the amplified DNA. The sample may then be sequenced using known sequencing technology, or the genetic type may be confirmed by performing sequence-specific amplification on the isolated sample, then determining the presence or absence of the genetic type by the presence or absence of a product from the sequence-specific amplification. A primer used in step (a) may include a label such as a fluorescent dye or radioactive isotope. The label is incorporated into the amplified DNA, and step (d) may then further comprise detecting the label, with or without an intervening step of removing the bound amplified DNA from the support.

To perform more comprehensive typing, steps (b) to (d) may be repeated with separate amounts of the amplified DNA using a different oligonucleotide bound to each support. The oligonucleotides undergo sequence specific hybridization under stringent conditions with complementary sequences of each known possible genetic type. In this manner, each possibility may be tested for at the same time. Alternately, the target molecules may be left attached to the initial probe on the support, and other labelled probes may be reacted with the target molecules in solution to detect key sequences. Oligotyping can be carried out with or without removal of the DNA from the support using labelled probes as described in, for example, the probe preparation methods described in U.S. Ser. No. 08/057,957, filed Apr. 8, 1993, now U.S. Pat. No. 5,702,885.

The step of analyzing the sample includes correlating the results with known alleles of the basic genetic type in a manner known to those skilled in the art. A process of elimination may be used to determine the allele or alleles present. In the first stage, the basic type is determined. The basic type may, however, include a number of confusingly similar "patchwork" alleles wherein newly discovered alleles often represent new combinations of known polymorphisms at different sites. HLA-DRB alleles, include many such patchwork alleles that are particularly difficult to resolve. In correlating the results to determine the allele present, it is often necessary to consider the results of several probe hybridizations, with different combinations of positive and negative results indicating different alleles. An allele may even be determined by negative inference, i.e., by a failure to positively detect any of the other possible alleles within the basic type. All of these strategies are contemplated by the present invention.

One preferred embodiment of the method of the invention includes the steps of:

(a) amplifying a genetic sequence of a subject to obtain amplified DNA, which genetic sequence occurs naturally in two or more basic genetic types, at least one of which types comprises two or more alleles;

(b) bringing a sample of the amplified DNA into contact with an oligonucleotide probe bound to a support under stringent hybridizing conditions, which oligonucleotide probe hybridizes specifically with DNA having a sequence of one of the basic genetic types and not with DNA having a sequence of the other basic genetic types;

(c) washing the support to remove unbound amplified DNA;

(d) then removing the bound amplified DNA from the support under conditions effective to isolate a sample of such amplified DNA; and (e) analyzing the sample to determine which allele is present.

The step (d) of removing the amplified DNA is preferably carried out by denaturing bound amplified DNA from the oligonucleotide probe sequence, applying a liquid vehicle to the denatured DNA, and removing the denatured DNA and liquid vehicle from the support. The removed DNA can then be sequenced using a commercially available automated sequencer, or typed by other known methods, such as sequence-specific amplification followed by electrophoresis to determine if amplified DNA is present. The removed DNA can also be subjected to conventional oligonucleotide probe typing, or to a second round of solid-phase oligonucleotide probe typing, which may then be followed by sequencing if needed to narrow down to a single allele.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DETAILED DESCRIPTION OF PREFERRED EMBODIMENTS

The method of the invention is particularly useful in typing human leukocyte antigens. In one embodiment, the invention provides a rapid method for identifying nucleotide sequences of polymorphic HLA genes. This aspect of the invention is particularly useful for tissue matching, especially for purposes of tissue transplantation.

Successful tissue transplantation, particularly bone marrow transplantation, depends on achieving a degree of HLA matching between donor/recipient pairs. This is true because of the physiological role played by human lymphocyte antigens in self-restriction of cellular interactions during and immune response. See Schwartz, Ann. Rev. Immunol. 3: 27–261 (1985). If the donor's and recipient's cells do not express the same HLA alleles, the immune system of the host may recognize the donor cells bearing the mismatched HLA proteins as foreign. The consequences of such mismatching include graft/host disease, graft rejection, and failure to reconstitute a competent immune system. These problems are minimized by selection of HLA-matched siblings as donors. Unfortunately, this option is available for only about 30–40% of patients who could benefit from a bone marrow transplant. In the remaining patients (60–70%), HLA typing with high resolving power is necessary for selection of an optimally matched, unrelated donor.

HLA-DR typing is particularly difficult because so many different DR types exist in the population, and more are being discovered on an ongoing basis. The 70 or so known HLA-DR alleles are split into major groups currently classified as HLA-DRB*01 to HLA-DRB*18, 51, 52 and 53. Each group has in common a polymorphism at a characteristic location. For example, the HLA-DRB1*08 basic type includes HLA-DRB1*0801, HLA-DRB1*08021, HLA-DRB1*08022, HLA-DRB1*08031, HLA-DRB1*08032, HLA-DRB1*0804, and HLA-DRB1*0805. These alleles, along with HLA-DRB1*1201, HLA-DRB1*1202 and HLA-DRB1*1404, share a unique sequence at positions 10–16 that differs from other known basic HLA-DRB types. See U.S. Ser. No 08/025,038, filed Mar. 1, 1993, now U.S. Pat. No. 5,545,526 and U.S. Ser. No. 08/057,957, filed Apr. 8, 1993, now U.S. Pat. No. 5,702,885, the contents of which applications are each incorporated by reference herein. However, each allele within the basic type differs from all others within the group at at least one polymorphic site.

The method of the invention permits the HLA type(s) present in an unknown sample to be determined, optionally without using sequence-specific amplification (SSA) as exemplified in Molkentin et al., cited above. Since an individual may have up to four different HLA-DR alleles, two from each parent, SSA becomes impractical as a way of detecting which basic DR types are present in an unknown sample. It may be necessary to run SSA many times to obtain the needed information, or use an alternative method, such as serological typing, before performing SSA.

The present method permits basic type identification in several simple steps, optionally followed by steps for determining the specific allele within the basic type. A sample of DNA to be typed is first amplified. The method of amplification employed is not critical and may be effected, for example, via the polymerase chain reaction (PCR) process or by self-sustained sequence replication (3SR); see generally Fahy et al., PCR Methods & Applications 1: 25–33 (1991), the contents of which are hereby incorporated by reference. PCR amplification is described in U.S. Pat. Nos. 4,683,195 and No. 4,683,202, the respective contents of which are hereby incorporated by reference. Modifications can be made, for example, in primer concentration, dNTP concentration, $Mg^{+2}$ concentration and thermal-cycling parameters, to optimize amplification.

The proper selection of primers is essential to the amplification step. The primers must hybridize to sequences that bracket the polymorphic nucleotide region of interest. Primers must hybridize with sufficient specificity to limit amplification (logarithmic synthesis) to the desired targets, and must hybridize with all alleles associated with the target polymorphic gene. If PCR is used, the effectiveness of primers is a function of the sequence of the primers as well as the reaction conditions for the polymerase chain reaction, e.g., temperature and time of annealing, temperature and time of denaturation, and salt concentration.

Samples of the amplified DNA are brought into contact with oligonucleotide probes that have been previously bound to a solid support, such as wells of a plastic dish, or microbeads suspended in a series of tubes; for known binding techniques, see Saiki et al., 1989, Proc. Natl. Acad. Sci. USA 86:6230 and Lund et al., 1988, Nucleic Acids Res. 17:4937. The latter form of support may be useful in keeping the different hybridization samples separate. Sequence-specific hybridization occurs between the amplified DNA and the probe sequence. The stringency of conditions is such that only amplified DNA matching the probe sequence hybridizes with the probe, and non-specific hybridization is avoided. Conditions that encourage formation of secondary structures in the amplified DNA should be avoided.

If the solid support comprises beads, particularly plastic microbeads having a magnetically attractable core for ease of separation, the beads are placed in test tubes such that each test tube contains the same probe. If the wells of a plate provide the solid support, each well contains the same probe. The first set of oligonucleotide probes, a different one in each tube or well, are preferably selected to classify the amplified target DNA into subsets of alleles associated with the target polymorphic gene.

Preferred beads for providing the solid support for the oligonucleotide probes are Dynabeads (styrene beads which have magnetite cores) which are uniform in size (about 4.5 $\mu$m) and display low particle-particle interaction. The beads are available commercially with a variety of active groups, including —OH (M450), —NH$_2$ (R240, R442, R469) and —COOH (R452). Synthetic oligonucleotides can be attached to an amino bead using a phosphoramidite linkage according to the method of (Gosh, S. S.; Musso, G. F., 1987 Nucleic Acids Research 15:5373). The foregoing three amino beads have been tested for their ability to bind oligonucleotides, and R469 bound the most DNA, presumably because the length of the linker (8 atoms) was optimal (Lund et al., 1988 Nucleic Acids Research 16:10861.)

Prehybridization of beads prior to oligonucleotide binding is preferably carried out as described by Lund et al. as a 30-to-60 minute incubation in 5×SSPE (20×SSPE is 0.17M sodium phosphate, pH 7.4, 3 M sodium chloride and 0.02 M EDTA), 10×Denhardts (1 g Ficoll, 1 g polyvinylpyrrolidone, and 1 g BSA in 500 ml water), 0.1% SDS and 1 g/l sonicated and denatured DNA. Prehybridization agents present in the foregoing solutions adhere to active sites on the bead surfaces and thereby prevent later non-specific binding of the amplified DNA to the bead surface.

A label such as a dye or radioactive isotope may be advantageously be incorporated into the amplified DNA, preferably as part of the primer sequence, even if the label will not ultimately be relied for typing, as when the bound DNA will later be removed and sequenced. In practice, a panel of supports each provided with a different probe sequence representing each basic type (such as DR1, DR2, DR3, etc.) will be used. Most will prove negative, since the unknown sample from a human subject will represent no more than four HLA DR types. Detection of the label can determine which of the tubes or wells contain bound DNA and which do not, eliminating the need to attempt to sequence or otherwise analyze supports that contain no bound DNA. Fluorescent label dyes are discussed further below.

Binding between the probe sequence and the support may be accomplished by labelling the probe sequence, generally at one end thereof, with one member of a pair of specific binding substances, e.g., biotin and streptavidin. The other of the pair is coated onto the support surface to which it naturally adheres. When the beads and probes are mixed in solution, specific binding occurs between the binding substances, adhering the probe sequences to the support. See Fry et al., *Biotechniques*, Vol. 13, No. 1 (1992).

In this connection, it may be useful to enlarge the probe somewhat over comparable probe sequences used in conventional oligotyping to permit, among other things, more freedom for binding. Probe sequences preferably range from 12 to 30 bases, particularly 12 to 24 bases. If needed, a short, non-binding nucleotide sequence may be interposed between the probe sequence and the binding substance.

The amplified target DNA is placed in each well or tube under suitable hybridization conditions. The exact temperature for hybridization with the labelled, amplified target DNA will be determined for each probe by methods known in the art. Temperature and salt concentration are exemplary of the factors that typically are considered. These conditions will be designed to permit later removal of all DNA that is not perfectly matched with the probe.

Once the amplified DNA and probes have incubated for a sufficient time, the support is washed in order to remove unbound DNA. In particular, the beads to which the probe is bound are washed under conditions that discriminate single base-pair mismatches between probes and labeled amplified target DNA. The beads having amplified DNA of the target basic type bound thereto by means of the probe are then resuspended in solution, and conditions are adjusted in order to denature the bound amplified DNA. This may be done by heating, for example, to a temperature of about 70° C., or by adding a base such as NaOH. Non-specifically bound DNA remains tightly bound to the beads under a variety of stringent conditions; it is unlikely, therefore, that any non-specifically bound DNA will be removed by incubation at temperatures that will denature the probe-amplified target DNA hybrid. The denatured DNA is then separated from the support. In the case of microbeads, filtration or magnetic removal of the beads may be used.

Controls should be included to monitor the specificity of the hybridization and the possibility of contaminating DNA originating from the reagents used to isolate the DNA, as well as to monitor the amplification method such as PCR or 3SR. One of the controls is a consensus probe specific to all alleles associated with the target polymorphic gene. The amplified target DNA should bind to the consensus probe regardless of the genetic type of type of the sample.

Identification of individual alleles is determined by comparing the hybridization pattern achieved to known hybridization patterns which correspond to individual alleles. Where the amplified target DNA exhibits a novel hybridization pattern, it will be advantageous to sequence the amplified target DNA directly. In an embodiment in which amplified target DNA is hybridized to a first set of oligonucleotide probes bound to beads, the amplified DNA hybridized to the probes can be denatured to provide highly purified, single-stranded DNA for subsequent sequence analysis.

According to an alternative embodiment of the invention, at least one of the primers used during the initial amplification is labeled, thereby obtaining at least one labelled amplified DNA strand of the target sequence. Where it is desirable to label both of the amplified DNA strands of the target sequence, both of the primers contain a label. The primer(s) are preferably labelled with fluorescent dyes which do not interfere with automated sequencing of the amplified target sequence. Thus, dyes which do not have the same emission or excitation properties as the sequencer dyes are used if the amplified bound sequence will be subsequently denatured and removed for sequencing. However, in the alternative, the amplified DNA that hybridizes to the probe on the support may remain on the support, i.e., is not denatured and removed for further analysis. Instead, a variety of techniques can be used to further analyze the bound DNA, as described hereafter.

At this stage, whether or not denaturation is carried out, the label may be observed to determine which basic types are present in the subject. If the label is a fluorescent dye, the individual supports may be examined visually or microscopically while exposing each to light of a wavelength that causes the dye to fluoresce, generally long-wave ultraviolet light, or an automated light detector may be used. Suitable fluorescent dyes that are incorporated into reagents used for automated sequencing are 4',5'-dichloro-2',7'-dimethoxy-6-carboxytetramethylrhodamine ("JOE"), 5'-carboxyfluorescein ("FAM"), 6-carboxytetramethylrhodamine (TAMRA), and 6-carboxy-X-thodamine ("ROX"). JOE and FAM fluoresce green and TAMRA and ROX fluoresce red.

A dye which fluoresces blue, 7-amino-4-methylcoumarin-3-acetic acid (COUM), can be used to label the amplified DNA. This can be accomplished by synthesizing oligonucleotides with a primary amino group attached to the 5' end, incubating the crude oligonucleotide mixture (3 O.D. units) at room temperature with 6 $\mu$l of COUM (83.3 g/ml) in dimethyl sulfoxide, and carrying out the conjugation reaction in 0.22M $NaHCO_3$, $Na_2CO_3$ at pH 9.0 for three hours. Most of the unconjugated dye will be separated from the non-labelled oligonucleotides by HPLC. Chehab and Kan (Chehab, F. F., Kan, Y. W., 1989, Proc. *Natl. Acad. Sci. USA* 86:9178) used an Aquopore 300-C8 column in two consecutive gradients of acetonitrile in 0.1 M triethylamine acetate (pH 7.0): 8–20% for 24 minutes and 20–40% for 10 minutes. The solvent is removed from the labelled oligonucleotide and the final product is resuspended in water. Once the dye has been selected, the PCR conditions can be determined empirically for the primers to ensure that the introduction of the dye does not have any effect on the specificity or efficiency of the PCR reactions.

Samples of the amplified, specifically bound DNA may then be further analyzed by contacting the samples with a second group of labeled probes under hybridizing conditions. Each of the second set of labelled probes detects a polymorphic sequence associated with the subset of alleles identified from the first stage, which functions as a low resolution assay for identifying the basic type. The second set of probes is designed to resolve the subsets of alleles identified from the low resolution assay into individual alleles. Identification of alleles is determined by comparing the hybridization pattern to known hybridization patterns for the alleles. The labels for the second stage may constitute dyes or radiolabels different from the first label.

The exact temperature for hybridization with the first hybrids obtained from the low resolution assay will be determined for each of the second set of probes using techniques within the ordinary skill in the art. Factors that need to be considered include temperature, solvent and salt concentration. These conditions will be designed to remove all DNA that is not perfectly matched with each of the second set of probes. If the second hybrids are formed with the first hybrids still bound to the support, it may prove necessary to ensure that the first hybrids do not dehybridize under the conditions used to form the second hybrids. For this purpose, the first hybrids may be cross-linked, for example by chemical or UV treatment, so that the first hybrids become irreversible and do not dehybridize. The resulting second hybrids formed between any of the second set of probes and the first hybrids obtained from the low resolution assay are then washed under conditions to discriminate any single base-pair mismatches.

As discussed above, the analyzing step may also be carried out by sequencing the sample directly, particularly if it is known in advance that the amplified product is not a mixture. Sequencing mixtures of DNA of closely similar alleles which may differ by only a single base pair can result in ambiguous or mistaken results. sequencing maybe carried out in a conventional manner using a commercially available automated sequencer, for example an ABI 373 sequencer, using available kit protocols, for example, Taq Dye Deoxy Terminator or Taq Dye Primer Cycle Sequencing available from Applied Biosystems.

The method of the invention is illustrated by the following example. In the example, a mixture of DR 4 and DR 8 PCR product was denatured and hybridized to streptavidin-coated magnetic beads containing a probe for DR 4 or DR 8 or no probe at all. The beads were washed and the DNA strands that bound the beads were eluted by heating at 80° C. for 5 minutes. DR 4 or DR 8 sequences were detected using sequence-specific PCR amplification. The results demonstrate that the DR 4 probe beads specifically bound DR 4 sequences, while the DR 8 probe beads specifically bound DR 8 sequences, and that the target sequences can subsequently be removed by denaturation for further analysis.

EXAMPLE

Oligonucleotide probes specific for DR 8/12 (PR 44) or DR 4 (PR 48) and biotinylated at the 5' end were synthesized with an ABI synthesizer and a biotin phosphoramidite (Clontech). Sequences for the probes were:

| Name | Sequence | DRB | Codons |
|---|---|---|---|
| PR 44 (SEQ ID NO:1) | 5'-TACTCTACGGGTGAGTGTT-3' | 8/12 | 10–16 |
| PR 48 (SEQ ID NO:2) | 5'-TTCTTGGAGCAGGTTAAAC-3' | 4 | 7–13 |

Streptavidin-coated magnetic beads (Dynal), 20 µl, were washed with 5 mM Tris-HCl pH 7.5, 0.5 mM EDTA, 1.0 M NaCl then incubated with biotinylated probes (PR 44 or PR 48) for 15 minutes at room temperature. The beads were washed with Tris/NaCl buffer followed by 6×SSC (0.9M NaCl, 0.09M sodium citrate) then prehybridized in a solution containing 6×SSC, 0.1% SDS, 5×Denhardt's solution and 100 pg/ml denatured herring sperm DNA at 37° C. for 30 minutes. The beads were resuspended in 40 µl of 2×hybridization buffer, then divided into two 20 µl aliquots.

DNA amplified from genomic DNA templates isolated from cell lines characterized during the 10th International Histocompatibility Workshop was hybridized to the probes that were attached to the magnetic beads. DNA (2 µg) from cell line 9029 (DR 4) and known cell line 9069 (DR 8) was amplified using primers PCR 38 and PCR 5 in a 175 µl reaction volume. The primer sequences were 5'-GTCCCCACAGCACGTTTCTTG-3' (SEQ ID NO:3) for primer PCR 38 5'-CGCCGCTGCACTGTGAAGCTCTC-3' (SEQ ID NO:4) for primer PCR 5. Twenty microliters of each PCR reaction product were mixed together, heated at 95° C. for 8 minutes in a PCR 480 heat block. The sample was stored on ice until ready for use.

A mixture of 10 µl of each water and DNA was added to each aliquot of beads. Water was substituted for DNA in the negative controls. The DNA and beads were incubated at 50° C. for 1.5 hr in a heat block, mixing the tubes every 15 to 20 minutes. All washes were carried out with the aid of a Dynal magnet. The beads were washed twice with 6×SSC 0.1% SDS, twice with 6×SSC and once with 2×SSC. The beads were resuspended in 40 µl of water and the DNA strands were eluted by heating at 80° C. for 5 minutes. The supernatant was recovered.

Sequence-specific PCR was carried out as described by Olerup and Zetterquist (*Tissue Antigens* 39:225). PCR reactions that detect either DR 4 or DR 8 sequences were used to analyze the eluted strands. The primer sequences were:

DR 4

5'04 (SEQ ID NO:5)
5'-GTTTCTTGGAGCAGGTTAAACA-3'

3'047 (SEQ ID NO:6)
5'-CTGCACTGTGAAGCTCTCAC-3'

3'048 (SEQ ID NO:7)
5'-CTGCACTGTGAAGCTCTCCA-3'

DR 8

5'08 (SEQ ID NO:8)
5'-AGTACTCTACGGGTGAGTGTT-3'

3'045 (SEQ ID NO:9) 5'-TGTTCCAGTACTCGGCGCT-3'

3'14 (SEQ ID NO:10)
5'-GCTGTTCCAGTACTCGGCAT-3'

The 3' primers were employed as a mixture for each respective DR 4 and DR 8 sample. The cycling conditions were 94° C. 20 sec, 65° C. 50 sec and 72° C. 20 sec. The number of PCR cycles varied between 9 and 15. Both products would be detected if too many PCR cycles were carried out. The reaction products were analyzed by 2% agarose gel electrophoresis and ethidium bromide staining. Lanes for electrophoresis were as described in Table 1 below.

TABLE 1

| Lane | Description of Agarose Gel | Result |
|---|---|---|
| 1 | Molecular weight standards, 100 bp ladder | Control-Positive |
| 2 | Blank, negative control | Negative |
| 3 | 9029/9069 DNA used for hybridization, DR 4 reaction → positive control | Positive |
| 4 | 9029/9069 DNA used for hybridization, DR 8 reaction → positive control | Positive |
| 5 | Eluted DNA from beads with no probe, DR 4 reaction. | Negative |
| 6 | Eluted DNA from beads with no probe, DR 8 reaction | Negative |
| 7 | Eluted DNA from beads with the DR 8 probe, no DNA in hybridization, DR 4 reaction → negative control | Negative |
| 8 | Eluted DNA from beads with the DR 8 probe, no DNA in hybridization, | Negative |

TABLE 1-continued

| Lane | Description of Agarose Gel | Result |
|---|---|---|
| | DR 8 reaction → negative control | |
| 9 | Eluted DNA from beads with the DR 8 probe, DR 4 reaction | Negative |
| 10 | Eluted DNA from beads with the DR 8 probe, DR 8 reaction | Positive |
| 11 | Eluted DNA from beads with the DR 4 probe, no DNA in hybridization, DR 4 reaction → negative control | Negative |
| 12 | Eluted DNA from beads with the DR 4 probe, no DNA in hybridization, DR 8 reaction → negative control | Negative |
| 13 | Eluted DNA from beads with the DR 4 probe, DR 4 reaction | Positive |
| 14 | Eluted DNA from beads with the DR 4 probe, DR 8 reaction | Negative |

Lanes 3 and 4 demonstrate that the sequence-specific PCR detected both the DR 4 and DR 8 sequences in the mixture of DNA used for the hybridization. Lanes 5 and 6 show that if no probe is on the bead, no DNA is recovered. Lanes 7, 8, 11 and 12 demonstrate that if DNA is not included during the hybridization on either the DR 4 or DR 8 specific bead, no DNA is recovered. Lanes 9 and 10 show that the DR 8-specific bead selectively recovers the DR 8 strand (lane 10) over the DR 4 strand (lane 9). Lanes 13 and 14 demonstrate that the DR 4-specific bead selectively recovers the DR 4 strand (lane 13) over the DR 8 strand (lane 14). The results thus show successful allele-specific DNA strand capture using biotinylated oligonucleotide probes bound to streptavidin-coated magnetic beads, followed by release of the captured DNA for subsequent analysis by techniques such as SSA or sequencing.

While the invention has been described in detail and with reference to specific embodiments thereof, various changes and modifications can be made therein without departing from the spirit and scope thereof. For example, the method of the invention can be used to identify HLA alleles, including HLA-DR and HLA-DQ alleles using in HLA typing, as discussed above, but is applicable to any similar kind of genetic typing operation.

I claim:

1. A method for genetic typing, comprising:
   (a) amplifying a genetic sequence of a subject to obtain amplified DNA, which genetic sequence occurs naturally in two or more alleles each characterized by multiple polymorphisms;
   (b) bringing a sample of the amplified DNA into contact with an oligonucleotide probe bound to a support under stringent hybridizing conditions under which only perfect matches hybridize, which oligonucleotide probe hybridizes specifically with a DNA sequence at which a polymorphism occurs in at least one of the alleles, so that amplified DNA of one allele binds specifically with the probe and amplified DNA of at least one other amplified allele does not bind specifically with probe;
   (c) removing unbound amplified DNA of the sample from the support under conditions that discriminate single base-pair mismatches between the probe and the amplified DNA so that only mismatching amplified DNA is removed;
   (d) then denaturing and removing bound amplified DNA from the support under conditions effective to isolate a sample of such amplified DNA; and
   (e) then further analyzing the isolated sample to detect one of more additional polymorphisms.

2. The method of claim 1, wherein the analyzing step (e) further comprises sequencing the isolated sample, and the amplified DNA of the sample in step (b) comprises a mixture of two or more of the alleles.

3. The method of claim 1, wherein the analyzing step further comprises performing sequence-specific amplification on the isolated sample, and determining the presence or absence of an additional polymorphism by the presence or absence of a product from the sequence-specific amplification.

4. The method of claim 1, further comprising repeating steps (b) to (e) with separate samples of the amplified DNA and with a plurality of supports, each comprising a different oligonucleotide, which oligonucleotides undergo sequence specific hybridization under stringent conditions under which only perfect matches hybridize with complementary sequences of alleles to be tested.

5. The method of claim 1, wherein the alleles each characterized by multiple polymorphisms comprise HLA alleles.

6. The method of claim 5, wherein the alleles each characterized by multiple polymorphisms comprise HLA-DR alleles.

7. The method of claim 1, wherein a pair of substances which undergo specific binding with each other are used to adhere the oligonucleotide probes to the support, one of the pair of substances being pre-adhered to the support and the other being bonded to the oligonucleotide probe, so that the probe is bound to the support when the pair of substances specifically bind to each other.

8. The method of claim 7, wherein the pair of substances comprise biotin and streptavidin.

9. The method of claim 7, wherein the support comprises microbeads.

10. The method of claim 1, wherein step (e) further comprises:

typing the isolated sample with one or more second, labelled oligonucleotide probes which hybridize under stringent conditions under which only perfect matches hybridize specifically with DNA having a sequence of one or more of the alleles at which a polymorphism occurs which is different from the polymorphism detected in step (b);

detecting the label to determine if hybridization has taken place between the isolated sample and each second oligonucleotide probe; and correlating the results with known alleles to determine which allele or alleles are present in the subject.

11. The method of claim 4, further comprising labelling the amplified DNA, and detecting which supports contain bound amplified DNA by observing the label.

12. The method of claim 11, further comprising labelling at least one primer used in step (a).

13. A method for HLA typing, comprising:

amplifying an HLA sequence of a subject to obtain amplified DNA, which HLA sequence occurs naturally in two or more HLA alleles each characterized by multiple polymorphisms, and the amplified DNA of the sample comprises a mixture of two or more HLA alleles;

bringing a sample of the amplified DNA into contact with an oligonucleotide probe bound to a support under stringent hybridizing conditions under which only perfect matches hybridize, which oligonucleotide probe hybridizes specifically with a DNA sequence at a location at which a polymorphism occurs in one of the HLA alleles so that amplified DNA of one HLA allele binds specifically with the probe and amplified DNA of other amplified HLA alleles does not bind specifically with the probe;

removing unbound amplified DNA of the sample from the support under conditions that discriminate single base-pair mismatches between he probe and the amplified DNA so that only mismatching amplified DNA is removed;

denaturing and removing bound amplified DNA from the support under conditions effective to isolate a sample of such amplified DNA; and then sequencing the isolated sample to identify the one HLA allele.

14. The method of claim 13, wherein the HLA alleles are HLA-DR beta alleles.

15. A method for HLA typing, comprising: amplifying an HLA sequence of a subject to obtain amplified DNA, which HLA sequence occurs naturally in two or more HLA alleles each characterized by multiple polymorphisms;

bringing a sample of the amplified DNA into contact with a first oligonucleotide probe bound to a support under stringent hybridizing conditions under which only perfect matches hybridize, which first oligonucleotide probe hybridizes specifically with a DNA sequence at a location at which a polymorphism occurs in at least one of the HLA alleles so that amplified DNA of at least one HLA allele binds specifically with the first probe and amplified DNA of at least one other HLA allele does not bind specifically with the first probe;

removing unbound amplified DNA of the sample from the support under conditions that discriminate single base-pair mismatches between the first probe and the amplified DNA so that only mismatching amplified DNA is removed;

denaturing and removing bound amplified DNA from the support under conditions effective to isolate a sample of such amplified DNA; and then further analyzing the isolated sample by typing the sample with a second oligonucleotide probe different from the first probe, which second probe hybridizes under stringent conditions under which only perfect matches hybridize specifically with DNA having a sequence of one or more of the HLA alleles at which a polymorphism occurs, which polymorphism is difference from the polymorphism detected by the first probe.

16. The method of claim 15, wherein the HLA alleles are HLA-DR beta alleles.

* * * * *

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
      (A) LENGTH: 19 base pairs
      (B) TYPE: nucleic acid
      (C) STRANDEDNESS: single
      (D) TOPOLOGY: linear (vii) IMMEDIATE SOURCE:
      (B) CLONE: PR 44

(xi) SEQUENCE DESCRIPTION: SEQ ID NO:1:

TACTCTACGG GTGAGTGTT          19

(2) INFORMATION FOR SEQ ID NO:2:

(i) SEQUENCE CHARACTERISTICS:
      (A) LENGTH: 19 base pairs
      (B) TYPE: nucleic acid
      (C) STRANDEDNESS: single
      (D) TOPOLOGY: linear (vii) IMMEDIATE SOURCE:
      (B) CLONE: PR 48

(xi) SEQUENCE DESCRIPTION: SEQ ID NO:2:

TTCTTGGAGC AGGTTAAAC          19

(2) INFORMATION FOR SEQ ID NO:3:

(i) SEQUENCE CHARACTERISTICS:
      (A) LENGTH: 21 base pairs
      (B) TYPE: nucleic acid

```
        (C) STRANDEDNESS: single
        (D) TOPOLOGY: linear (vii) IMMEDIATE SOURCE:
        (B) CLONE: PCR 38

(xi) SEQUENCE DESCRIPTION: SEQ ID NO:3:

GTCCCCACAG CACGTTTCTT G                                              21

(2) INFORMATION FOR SEQ ID NO:4:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (vii) IMMEDIATE SOURCE:
        (B) CLONE: PCR 5

(xi) SEQUENCE DESCRIPTION: SEQ ID NO:4:

CGCCGCTGCA CTGTGAAGCT CTC                                            23

(2) INFORMATION FOR SEQ ID NO:5:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (vii) IMMEDIATE SOURCE:
        (B) CLONE: DR 4 5'04

(xi) SEQUENCE DESCRIPTION: SEQ ID NO:5:

GTTTCTTGGA GCAGGTTAAA CA                                             22

(2) INFORMATION FOR SEQ ID NO:6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (vii) IMMEDIATE SOURCE:
        (B) CLONE: DR 4 3'047

(xi) SEQUENCE DESCRIPTION: SEQ ID NO:6:

CTGCACTGTG AAGCTCTCAC                                                20

(2) INFORMATION FOR SEQ ID NO:7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (vii) IMMEDIATE SOURCE:
        (B) CLONE: DR 4 3'048

(xi) SEQUENCE DESCRIPTION: SEQ ID NO:7:

CTGCACTGTG AAGCTCTCCA                                                20

(2) INFORMATION FOR SEQ ID NO:8:

(i) SEQUENCE CHARACTERISTICS:
        (A) LENGTH: 21 base pairs
```

```
            (B) TYPE: nucleic acid
            (C) STRANDEDNESS: single
            (D) TOPOLOGY: linear (vii) IMMEDIATE SOURCE:
             (B) CLONE: DR 8 5'08

(xi) SEQUENCE DESCRIPTION: SEQ ID NO:8:

AGTACTCTAC GGGTGAGTGT T                                                      21

(2) INFORMATION FOR SEQ ID NO:9:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (vii) IMMEDIATE SOURCE:
             (B) CLONE: DR 8 3'045

(xi) SEQUENCE DESCRIPTION: SEQ ID NO:9:

TGTTCCAGTA CTCGGCGCT                                                         19

(2) INFORMATION FOR SEQ ID NO:10:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (vii) IMMEDIATE SOURCE:
             (B) CLONE: DR8 3'14

(xi) SEQUENCE DESCRIPTION: SEQ ID NO:10:

GCTGTTCCAG TACTCGGCAT                                                        20
```